United States Patent [19]

Rosenkranz et al.

[11] 4,053,504

[45] Oct. 11, 1977

[54] STABILIZED ACRYLIC ACID ESTERS OF POLYHYDRIC ALCOHOLS AND A PROCESS FOR THEIR PREPARATION

[75] Inventors: Hans Jürgen Rosenkranz; Hans Rudolph; Gerhard Apel, all of Krefeld, Germany

[73] Assignee: Bayer Aktiengesellschaft, Germany

[21] Appl. No.: 695,533

[22] Filed: June 14, 1976

[30] Foreign Application Priority Data

June 18, 1975 Germany .............................. 2527005

[51] Int. Cl.$^2$ ............................................. C07C 69/52
[52] U.S. Cl. ........................................ 560/4; 560/224
[58] Field of Search ........................................ 260/486

[56] References Cited

U.S. PATENT DOCUMENTS 3,959,358   5/1976   Jurisch ............................ 260/486 R Primary Examiner—James O. Thomas, Jr.
Assistant Examiner—Lisa Jones
Attorney, Agent, or Firm—Connolly and Hutz

[57] ABSTRACT

Stabilized acrylic acid esters of polyhydric alcohols which contain as stabilizers polymerisation inhibitors including small amounts of compounds of the styrene type show a non-reduced polymerisation reactivity.

8 Claims, No Drawings

STABILIZED ACRYLIC ACID ESTERS OF POLYHYDRIC ALCOHOLS AND A PROCESS FOR THEIR PREPARATION

The invention relates to stabilised, polymerisable acrylic acid esters with at least two acrylic acid radicals and a process for their preparation from compounds which have several hydroxyl groups capable of esterification, and acrylic acid.

Acrylic acid esters of polyhydric alcohols show a very high tendency towards undesirable polymerisation. Therefore, polymerisation inhibitors which are in themselves known, such as phenols, phenol derivatives, copper, copper compounds and phenothiazine, have already been used to stabilise these compounds; however, these additives generally prove to be inadequate, especially in the most critical phase, that is the preparation of the acrylic acid esters.

Thus, it is known from DT-AS (German Published Specification) 1,267,547 and from Chem. and Ind. 18 (1970), page 597 to prepare acrylic acid esters of polyhydric alcohols by azeotropic esterification of acrylic acid with polyhydric alcohols in the presence of the said polymerisation inhibitors and of acid catalysts, for which reaction concentrated sulphuric acid has been used as the acid catalyst and benzene has been used as the entraining agent for the water of reaction. This process has the disadvantage that premature polymerisation during the esterification can be prevented only by carrying out the process in the presence of relatively large amounts of these inhibitors, which greatly reduce the reactivity of the acrylic acid esters of polyhydric alcohols and thus make the preparation of polymerisation products from the monomeric compounds considerably more difficult.

It has now been found that small amounts of certain unsaturated costabilisers in combination with known polymerisation inhibitors are outstandingly suitable for the stabilisation of acrylic acid esters of polyhydric alcohols against undesirable polymerisation, especially during the preparation phase.

The invention thus relates to acrylic acid esters of polyhydric alcohols which are stabilized by means of polymerisation inhibitors which include small amounts of unsaturated compounds of the formula

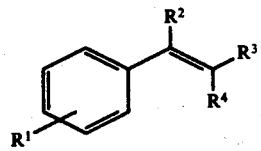

wherein
$R^1$ denotes a hydrogen atom, alkyl with 1 to 4 C atoms, chlorine or alkoxy with 1 to 4 C atoms,
$R^2$ denotes a hydrogen atom or alkyl with 1 to 4 C atoms,
$R^3$ and $R^4$ denote a hydrogen atom, $CH_2OH$, $CH_2$—O—A,

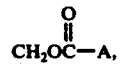

CHO, COOH, COO—A, $CONH_2$, CONH—A, CONH—Ar, $CH_2Cl$, $CH_2Br$ or CN.

A denotes an alkyl radical with 1 to 6 C atoms and
Ar denotes an aryl radical with 6 to 15 C atoms.

The acrylic acid esters of polyhydric alcohols contain 0.001 – 5% by weight, preferably 0.01 – 1% by weight, of costabilisers and preferably 0.01 – 0.3% by weight of polymerisation inhibitors which are in themselves known, the precentages being calculated relative to acrylic acid esters of polyhydric alcohols.

A further subject of the invention is a process for the preparation of stailised acrylic acid esters of polyhydric alcohols comprising esterifying acrylic acid with compounds which contain several hydroxyl groups capable of esterification, the esterification being carried out in the presence of samll amounts of costabilisers according to the above formula in combination with other polymerisation inhibitors.

Suitable compounds which have several hydroxyl groups capable of esterification are virtually all the polyols customarily used in the chemistry of polyesters. Examples which may be mentioned are dihydric and higher than dihydric, especially dihydric, trihydric and tetrahydric, aliphatic and cycloaliphatic alcohols, the aliphatic radicals of which can contain oxygen atoms as chain members, especially those radicals with 2 to 20 carbon atoms. Examples which may be mentioned are ethylene glycol, propylene glycol, butanediol, hexanediol, neopentyl glycol, diethylene glycol, triethylene glycol, dimethylolpropane, dimethylolcyclohexane, glycerol, trimethylolpropane, trimethylolhexane, trimethylolethane, hexane-1,3,5-triol, pentraerythritol, dipentaerythritol and tripentaerythritol, mannitol and sorbitol. Polyethers, which contain hydroxyl groups, of dihydric and higher hydric alcohols and polyesters of polyhydric alcohols and polybasic carboxylic acids are also suitable.

The compounds containing hydroxyl groups and mixtures of these compounds can be esterified with acrylic acid in equivalent amounts but it can be desirable, for example when using polyhydroxy compounds with more than two hydroxyl groups, such as trimethylolpropane or pentaerythritol, or in the case of sugar alcohols, to esterify with acrylic acid only some of the hydroxyl groups which are present. In this case it is possible to employ less than the equivalent amount of acrylic acid. However, the use of excess acrylic acid for the esterification is also possible in principle. Complete esterification of all the hydroxyl groups which are present can already be achieved with an excess of about 10 mol per cent above the theoretically required amount. The excess acrylic acid can remain in the reaction mixture or it can be removed or reacted in various ways after the esterification, for example by a reaction with an epoxy compound. It is also possible to remove excess acrylic acid by an extraction by means of a basic aqueous solution.

Suitable polymerisation inhibitors which are in -hydroxy-benzyl)benzene, knwon are, for example, phenols and phenol derivatives, preferably sterically hindered phenols which contain alkyl substitutents with 1 to 6 C atoms in the two positions ortho to the phenolic hydroxyl groups, amines, preferably secondary arylamines and their derivatives, quinones, copper salts of organic acids and addition compounds of copper-I halides with phosphites, such as, for example, 4,4′-bis-(2,6-di-tert.-butylphenol), 1,3,5-trimethyl-2,4,6-tris-(3,5-di-tert.-butyl-4,-hydroxy-benxyl)-benzene, 4,4′-butylidene-bis-(6-tert.-butyl-m-cresol), 3,5-di-tert.-butyl-4-hydroxy-benzylphosphonic acid diethyl ester, N,N′-bis-(β-naphthyl)-p-phenylenediamine, N,N'-bis-(1-methylheptyl)-p-phenylenediamine, phenyl-β-naphthylamine, 4,4'-bis-(α,α-dimethylbenzyl)-diphenylamine, 1,3,5-tris-(3,5-di-tert.-butyl-4-hydroxy-hydrocinnamoyl)-hexanehydro-s-triazine, hydroquinone, β-benzoquinone, toluhydroquinone, p-tert.-butylpyrocatechol, chloranil, naphthoquinone, copper naphthenate, copper octoate, Cu-(I)Cl/triphenyl phosphite, Cu(I)Cl/trimethyl phosphite, Cu(I)Cl/trischloroethyl phosphite, Cu(I)Cl/tripropyl phosphite and p-nitrosodimethylaniline. The use of hydroquinone monomethyl ether and phenothiazine is preferred. Other suitable stabilisers are described in "Methoden der organischen Chemie" ("Methods of Organic Chemistry") (Houben-Weyl), 4th edition, volume XIV/1, page 433–452 and 756, Georg Thieme-Verlag, Stuttgart, 1961. The inhibitors are generally added to the reaction mixture before the start of the esterification process, in amounts of from 0.01 to 0.3% by weight, calculated relative to the mixture of acrylic acid and polyhydroxy compound.

The unsaturated costabilisers employed according to the invention are extremely effective additional stabilisers; without these it has hitherto not been possible, or has been possible only with great effort, to obtain acrylic acid esters of polyhydric alcohols which have no gel contents or turbidity and, at the same time, are of high reactivity.

This finding is the more surprising since, as is known, many of the unsaturated compounds which can be used here, for example styrene and its derivatives, can themselves be polymerised by a radical mechanism. A stabilising effect, especially when the preparation is carried out at elevated temperature by esterification, is surprising and was not foreseeable for the additives according to the invention.

Specific examples of suitable costabilisers are styrene, α-methylstyrene, 4-tert.-butylstyrene, 4-chlorostyrene, cinnamic acid, cinnamaldehyde, cinnamic alcohol, p-methoxycinnamic acid, p-methoxycinnamaldehyde, p-methoxycinnamic alcohol, cinnamyl chloride, cinnamic acid methyl ester, cinnamic acid ethyl ester, cinnamic acid amide and cinnamic acid anilide. Compounds which under the reaction conditions for the esterification of acrylic acid supply the costabilisers according to the invention, for example α,α-dimethylbenzyl alcohol, can also be employed.

Preferred costabilisers to be singled out in particular from this list are cinnamic alcohol, cinnamaldehyde and cinnamic acid. The stabilising action of polymerisation inhibitors and costabilisers is even further increased by atmospheric oxygen.

The esterification process according to the invention is preferably carried out under azeotropic conditions in the presence of an aliphatic hydrocarbon or hydrocarbon mixture with a boiling range between 40° and 80° C, preferably of 50° 70° C, as the entraining agent. Preferably, the reaction is carried out under an atmosphere of air. A point to be singled out in particular is that the actual reaction mixture, consisting of polyhydric alyohol and acrylic acid is immiscible with this solvent at least at a relatively low temperature.

Examples of aliphatic hydrocarbons which are suitable as entraining agents are hexane and its isomers and cyclohexane, but above all hydrocarbon mixtures, which can also contain hydrocarbons with higher or lower boiling points, such as pentane or heptane and which boil in the desired temperature range. The amount of the hydrocarbon or hydrocarbon mixture which is added is in no way critical; depending on the equipment used in which the esterification is carried out, the amount added can be selected between 0.05 times and 2 times by weight the amount of the reaction mixture. A ratio of 1 part by weight of esterification mixture to 0.1 to 0.5 part by weight of hydrocarbon or hydrocarbon mixture is advantageous.

As the esterification proceeds, the hydrocarbons serve as auxiliaries in order to remove the water which is liberated. The esterification in the sense of the invention must thus be carried out under conditions, in respect of apparatus, under which it is possible to separate off the water of reaction in this way. Usually a conventional water separator is used for this purpose.

The catalysts used for the process, according to the invention, for the preparation of stabilised acrylic acid esters of polyhydric alcohols are, for example, commercially available acid ion exchange resins, preferably those which contain sulphonic acid groups as the ion exchange groups. They can be employed in an amount which is 0.005 to 1 times, preferably 0.05 to 0.2 times by weight that of the reaction mixture. Sulphonic acids, for examples -toluenesulphonic acid or benzenesulphonic acid, as well as sulphuric acid, can also be added as esterification catalysts. The requisite amounts are between 0.01 and 2% by weight, based on the reaction mixture.

A typical method for preparing the stabilised acrylic acid esters according to the invention is, for example, to heat a mixture of acrylic acid, polyhydroxy compound and polymerisation inhibitor, the latter including the costabiliser according to the invention, together with an acid ion exchanger and the amount of hydrocarbon mixture required to separate off the water, under reflux in a stirred vessel, which can be heated and which has a device for azeotropic separation of water. The amount of water which is separated off and the fall in the free acrylic acid content, which can easily be determined by titration, give information on the progress of the esterification reaction. When the free acrylic acid content has reached the desired value, the reaction is discontinued and the hydrocarbon mixture which serves as an entraining agent for the water of reaction is distilled off. Any remaining hydrocarbon mixture can be removed under reduced pressure. The acid ion exchanger is removed by filtration and the acrylic acid ester according to the invention is ready for use as a lacquer raw material for electron beam curing, in printing inks which can be cured by UV light, for plastic printing plates or in moulding compositions or casting compositions. However, the use of these products is in no way restricted to the applications mentioned here; in principle, they can be employed wherever acrylic acid esters or methacrylic acid esters of polyhydric alcohols have also been employed hitherto.

When carrying out the esterification process according to the invention, a washing process in order to remove the esterification catalyst is unnecessary in many cases; stabilisation with stailisers, which reduce the reactivity, of the conventional type, for example phenolic compounds or copper compounds, can be reduced to a level which has no adverse effect on the reactivity of the product. Moreover, the present process enables the acrylic acid esters of polyhydric alcohols to be prepared on an industrial scale. Even with batches of the order of size of several tonnes, the esterification can be carried out without problems in the manner indicated here.

If an acid which is soluble in the reaction mixture, for example p-toluenesulphonic acid or sulphuric acid, is used as the esterification catalyst, it is advisable, after the reaction is complete, to add, for neutralisation, an appropriate amount of a base, for example sodium carbonate, barium carbonate or similar agents which form salts which can be filtered off. The acid catalyst can also be removed together with excess acrylic acid by extraction.

With a washing process of this type it is also possible, if cinnamic acid or corresponding acid compounds are used as the costabiliser, largely to extract these at the same time, so that the stabilising effect is restricted exclusively to the critical esterification process.

A further advantage of the process according to the invention arises, surprisingly, from the fact that the reactants acrylic acid and polyhydroxy compound are immiscible with the hydrocarbon or hydrocarbon mixture. Comparison with an esterification in benzene shows that the rate of esterification is considerably increased. This fact is also of advantage for industrial utilisation of the process according to the invention.

It is also possible to carry out the process continuously, taking into account the criteria according to the invention. By continuously feeding in acrylic acid, polyhydroxy compound, polymerisation inhibitors, costabilisers and hydrocarbon (mixture) and, at the same time, removing the completely esterified product, it is possible to set up a stationary state which, because of the very good heat stability of the acrylic acid esters, according to the invention, of polyhydric alcohols, can be maintained for a virtually unlimited period without polymerisation occurring.

The invention will now be explained in more detail with the aid of the illustrative examples which follow. Percentage data to be found in the following text denote percentages by weight.

EXAMPLE 1

Butane-1,4-diol bis-acrylate

In a 25 l stirred kettle with a water separator, 6.76 kg of butane-1,4-diol, 10.8 kg of acrylic acid, 1.3 kg of an acid ion exchanger (Lewatit 3333 from Bayer AG), 22.8 g of p-methoxyphenol, 88 g of cinnamic acid and also 3 l of a petroleum ether fraction which boils in a range from 60–70° C, were heated to the boil, whilst stirring and passing in air, under the water separator. After a period of 62 hours, in which the boiling point of the mixture had risen from an initial value of 63° C to a final value of 70° C, an acid number of 25 was determined by titrating a sample and the reaction was discontinued. Up to this time, 2.36 l of $H_2O$ had been separated off. The petroleum ether was distilled off, first under normal pressure and then under reduced pressure. The product was freed from esterification catalyst by filtration and the catalyst was used for further esterifications. 14.5 kg of a clear, virtually colourless butane-1,4-diol bisacrylate, which is of high reactivity when cured under the influence of electron beams, were obtained. The viscosity corresponded to a flow time of 11 seconds, measured according to DIN 53,211 in a DIN cup 4, at 20° C.

EXAMPLE 2

Trimethylolpropane tris-acrylate

In a 10 l three-necked flask with a stirrer, a water separator and a gas inlet tube, 2.44 kg of trimethylolpropane, 3.93 kg of acrylic acid, 0.5 kg of an acid ion exchanger (Lewatit 3333 from Bayer AG), 9 g of hydroquinone and also 19 g of styrene together with 1.5 l of petroleum ether (boiling range 60°–70° C) were heated, whilst stirring, under the water separator. During the esterification a slow stream of air was passed through the reaction. After 80 hours, the reaction mixture had an acid number of 32 and the boiling point had risen to 72° C. The petroleum ether was distilled off, residues being removed by applying a vacuum of 0.2 mm Hg at a product temperature of 40° C. The esterification catalyst was separated off by filtration. The trimethylolpropane trisacrylate, which was obtained in almost quantitative yield, was pale yellowish and clear. The viscosity corresponded to a flow time of 20 seconds, measured according to DIN 53,211 in a DIN cup 4, at 20° C. Even when stored for 4 months at 60° C, the product showed no change. When used in a printing ink, which can be cured by UV light, and which contained a photoinitiator, the product polymerised at a high rate.

EXAMPLE 3

In a 3 l three-necked flask with a stirrer, a water separator and a gas inlet tube, 402.5 g of trimethylolpropane, 648.5 g of acrylic acid, 0.53 g of p-methoxyphenol and 5.23 g of cinnamic alcohol, together with 200 ml of hexane, were heated under reflux, a slow stream of air being passed in. When the boiling point was reached, an amount of 0.6 g of concentrated $H_2SO_4$ in 2 ml of water was added and azeotropic esterification started. After 80 hours, the reaction mixture had an acid number of 40 and the boiling point was 75° C. After 100 hours an acid number of 25 was reached and the hexane was distilled off, residues being removed by applying a vacuum of 0.2 mm Hg at a product temperature of 40° C. The esterification catalyst was neutralised by adding 5 g of sodium carbonate and the batch was filtered. The virtually colourless trimethylolpropane tris-acrylate had a viscosity correspnding to a flow time of 20 seconds, measured according to DIN 53,211 in a DIN cup 4, at 20° C.

EXAMPLE 4

Trimethylolpropane tris-acrylate was prepared analogously to Example 3, using an equimolar amount of cinnamaldehyde as the costabiliser. In this case also the esterification proceeded without problems and without the precipitation of polymers. This product also displayed good storage stability of more than 3 months at 60° C.

EXAMPLE 5 (comparison)

When the esterification according to Example 3 was carried out without the addition of cinnamic alcohol, gel-like encrustations on the stirrer and the walls of the vessel already formed during the esterification. The product was turbid and at a storage temperature of 60° C already gelled after 2 days.

EXAMPLE 6

Butane-1,4-diol/trimethylolpropane mixed acrylate 4.03 kg of trimethylolpropane, 2.7 kg of butane-1,4-diol and 10.8 kg of acrylic acid were esterified, as described in Example 1, in the presence of 22 g of phenothiazine, 1.3 kg of an acid ion exchanger and 3 l of a light benzine fraction which boils at 60°–70° C, under a water separator. 150 g of α-methylstyrene were added as a costabiliser to the esterification mixture. 14.5 kg of a stabilised mixed acrylate with an acid number of 25 were obtained.

EXAMPLE 7

Analogously to Example 6, it is also possible to obtain a mixed ester of acrylic acid with trimethylolpropane and propane-1,3-diol. In this case the reaction time is prolonged to about 90 hours.

EXAMPLE 8

In a 1 l three-necked flask with a gas inlet tube, a stirrer and a water separator, 136.2 g of pentaerythritol, 288.3 g of acrylic acid, 2.5 g of styrene, 2.12 g of p-toluenesulphonic acid, 0.5 g of p-methoxyphenol and 110 ml of petroleum ether (fraction boiling at 60°–70° C) were heated to the reflux temperature, whilst passing air through the mixture. After an esterification time of 48 hours, the acid number of the mixture had reached 35. After evaporating off the petroleum ether and neutralising the esterification catalyst with 10 g of sodium carbonate, the pentaerythritol tetraacrylate was pressed through a KO filter. This gave a pale yellow clear product which, when used in a lacquer which can be cured by an electron beam, enabled high curing rates to be achieved.

EXAMPLE 9

Analogously to Example 1, a bis-acrylate was prepared from neopentylglycol and acrylic acid. Stabilisation was carried out with equimolar amounts of benzoquinone and p-methoxycinnamic acid.

EXAMPLE 10

Trimethylolpropane diacrylate

In a 10 l three-necked flask with a stirrer, a water separator and a gas inlet tube, 2.68 kg of trimethylolpropane, 3.03 kg of acrylic acid, 0.5 kg of an acid ion exchanger (Lewatit 3333 from Bayer AG), 9 g of hydroquinone monomethyl ether and 28.6 g of cinnamyl chloride, together with 1.5 l of petroleum ether (boiling range 60°–70° C) were heated under the water separator, whilst stirring. At the same time a continuous stream of air was passed through at a rate of about 2 l/hour. After a reaction period of 72 hours, an acid of 17 was reached. The petroleum ether was distilled off, residues being removed by applying a vacuum of about 4 mm Hg at a product temperature of 40° C. The esterification catalyst was filtered off. The resulting trimethylolpropane diacrylate mixture was pale yellowish and clear. The viscosity corresponded to a flow time of 186 seconds, measured according to DIN 53,211 in a DIN cup 4, at 20° C.

EXAMPLE 11

Hexanediol bis-acrylate

In a 3 l three-necked flask with a stirrer, a water separator and a gas inlet tube, 472 g of hexane-1,6-diol, 576 g of acrylic acid, 0.52 g of p-methoxyphenol, 5.2 g of cinnamic acid and 500 ml of n-hexane were heated to the reflux temperature, whilst passing air through the mixture. After the reflux temperature was reached, 3 g of 50% strength sulphuric acid were added and the esterification reaction started, water being eliminated. After 70 hours an acid number of 18 was reached. The mixture was cooled and the free acrylic acid which was still present and the esterification catalyst were removed by extracting 3 times with dilute aqueous sodium bicarbonate solution. The n-hexane was distilled off, finally under reduced pressure, and the resulting hexanediol bis-acrylate was finally pressed through a KO filter. This gave a colourless neutral hexanediol bis-acrylate which, when used in lacquer raw materials which can be cured in UV light, displays a high reactivity. The storage stability at 60° C was more than 4 months.

EXAMPLE 12

Analogously to Example 11, it is possible to obtain dimethylolpropane bis-acrylate from dimethylolpropane and twice the molar amount of acrylic acid, using styrene as the costabiliser. In this case also there is no gel formation whatsoever during the esterification and the product is colourless and clear.

We claim:

1. A composition comprising an acrylic acid ester of a polyhydric alcohol stabilized by
   a. 0.01 to 0.3% by weight, based on the weight of said ester, of a stabilizer selected from the group consisting of phenols, amines, quinones, copper salts of organic acids and addition compounds of copper-I halides and phosphites and
   b. 0.001 to 5% by weight, based on the weight of said ester, of a compound of the formula:

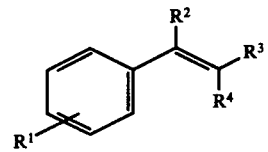

wherein $R^1$ is hydrogen, alkyl having 1 to 4 carbon atoms, chlorine or alkoxy having 1 to 4 carbon atoms, $R^2$ is hydrogen or alkyl having 1 to 4 carbon atoms and $R^3$ and $R^4$ are each hydrogen, $CH_2OH$, $CH_2-O-A$,

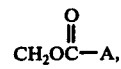

CHO, COOH, COO—A, $CONH_2$, CONH—A, CONH—Ar, $CH_2Cl$, $CH_2Br$ or CN wherein A is alkyl having 1 to 6 carbon atoms and Ar is aryl having 6 to 15 carbon atoms.

2. The composition of claim 1 wherein a is hydroquinone monomethyl ether.

3. The composition of claim 1 wherein a is phenothiazine.

4. A process for preparing a stabilized acrylic acid ester of a polyhydric alcohol which comprises esterifying acrylic acid with a polyol capable of esterification in the presence of
   a. 0.01 to 0.3% by weight, based on the weight of acrylic acid and polyol, of a stabilizer selected from the group consisting of phenols, amines, quinones, copper salts of organic acids and addition compounds of copper-I halides and phosphites and
   b. 0.001 to 0.5% by weight, based on the weight of acrylic acid and polyol, of a compound of the formula:

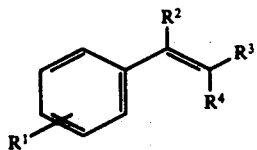

wherein $R^1$ is hydrogen, alkyl having 1 to 4 carbon atoms, chlorine or alkoxy having 1 to 4 carbon atoms, $R^2$ is hydrogen or alkyl having 1 to 4 carbon atoms and $R^3$ and $R^4$ are each hydrogen, $CH_2OH$, $CH_2-O-A$,

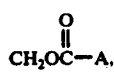

CHO, COOH, COO—A, $CONH_2$, CONH—A, CONH—Ar, $CH_2Cl$, $CH_2Br$ or CN wherein A is alkyl having 1 to 6 carbon atoms and Ar is aryl having 6 to 15 carbon atoms.

5. The process of claim 4 wherein the esterification is carried out under azeotropic conditions using at least one aliphatic hydrocarbon having a boiling point between about 40° and 80° C. as the entraining agent for by-product water.

6. The process of claim 4 wherein an acid ion exchanger is used as esterification catalyst.

7. The process of claim 6 wherein sulphuric acid or an organic sulphonic acid is used as esterification catalyst.

8. The process of claim 4 wherein the reaction is carried out in the presence of air.

* * * * *